United States Patent [19]
Bryant et al.

[11] Patent Number: 5,426,234
[45] Date of Patent: Jun. 20, 1995

[54] PHENYLETHYNYL TERMINATED REACTIVE OLIGOMER

[75] Inventors: Robert G. Bryant, Poquoson; Brian J. Jensen, Williamsburg; Paul M. Hergenrother, Yorktown, all of Va.

[73] Assignee: The United States of America as represented by the Administrator of the National Aeronautics and Space Administration, Washington, D.C.

[21] Appl. No.: 245,171

[22] Filed: May 16, 1994

Related U.S. Application Data

[62] Division of Ser. No. 45,343, Apr. 2, 1993, Pat. No. 5,312,994.

[51] Int. Cl.$^6$ .............................................. C07C 49/76
[52] U.S. Cl. ...................... 568/333; 568/33; 568/639
[58] Field of Search ............... 568/30, 31, 306, 332, 568/928, 570, 128, 333, 33, 639

[56] References Cited

U.S. PATENT DOCUMENTS

| | | | |
|---|---|---|---|
| 5,138,028 | 8/1992 | Paul et al. | 528/353 |
| 5,268,444 | 12/1993 | Jensen et al. | 528/125 |

*Primary Examiner*—James H. Reamer
*Attorney, Agent, or Firm*—George F. Helfrich

[57] ABSTRACT

A composition of matter having the general structure:

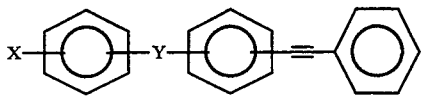

(wherein X is F, Cl, or $NO_2$, and Y is CO, $SO_2$ or $C(CF_3)_2$) is employed to terminate a nucleophilic reagent, resulting in the exclusive production of phenylethynyl terminated reactive oligomers which display unique thermal characteristics. A reactive diluent having the general structure:

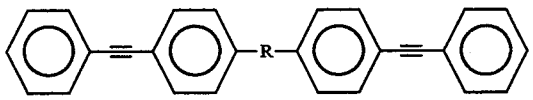

(wherein R is any aliphatic or aromatic moiety) is employed to decrease the melt viscosity of a phenylethynyl terminated reactive oligomer and to subsequently react therewith to provide a thermosetting material of enhanced density. These materials have features which make them attractive candidates for use as composite matrices and adhesives.

1 Claim, 5 Drawing Sheets

PHENYLETHYNYL TERMINATED REACTIVE OLIGOMER

CROSS REFERENCE TO RELATED APPLICATIONS

This is a divisional of application Ser. No. 08/045,343 filed on Apr. 2, 1993, now U.S. Pat. No. 5,312,994.

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

1. Field of the Invention

The present invention generally relates to specific compounds which display enhanced moderate thermal stability, but will undergo thermal reactions at higher temperatures. It relates particularly to chemical compounds which contain a phenylethynyl group, which can be used as terminating species to transform multifunctional nucleophiles into reactive materials that can be converted thermally into thermosets. It also relates to compounds containing di(phenylethynyl) groups that can be used as reactive diluents.

2. Description of Related Art

Oligomers and monomeric compounds have been endcapped with various reactive species to generate materials that can be processed into various shapes with or without reinforcements. Upon thermal activation, these materials crosslink without the evolution of volatiles to form high molecular weight intractable resins. The reactive functionalities used to endcap various multifunctional compounds include epoxies, acetylenes, cyanates, and maleimides. An article entitled "Acetylene Terminated Prepolymers" by P. M. Hergenrother, *Encycl. Polym. Sci. Eng.*, Vol. 1, 2nd Ed., John Wiley & Sons, Inc., New York, N.Y., (1985), p. 61, describes the use of ethynyl groups to endcap oligomers and the use of phenylethynyl groups along the polymer backbone.

More recently, B. Delfort et al., *J. Polym. Sci.*, Part A., 28, 2451, (1990), and 29, 897, (1991) used 4-ethynyl-4'-fluorobenzophenone, 4-ethynyl-4'-fluorodiphenylsulfone, and their respective chlorinated and nitrated analogs to endcap hydroxy terminated arylene-ethers. These reactive oligomers were thermally treated at 160° C. for 45 minutes then postcured at 250°–270° C. for 45 minutes to afford the arylene-ether thermosets. The reactive endcapping materials described in the Hergenrother article referred to above typically cure between 160° C. and 250° C. This limits both the thermal stability (pot life) of these systems at moderately elevated temperatures and the ability to decrease the melt viscosity at elevated temperatures. Also, these systems encounter problems of vitrification during the thermal curing cycle if the resulting material has a glass transition temperature (Tg) greater than the curing temperature. Thus, not only will these systems produce a material with a Tg no greater than that of the maximum curing temperature, but if the material has vitrified, it is unstable and a variation in the mechanical and thermal properties will occur throughout the life span of the material.

SUMMARY OF THE INVENTION

An object of the present invention is to provide a compound which can be used to endcap nucleophilic species such as hydroxyl and thiol functionalities.

Another object is to provide a reactive oligomer which is thermally stable at moderately high temperatures, but reacts at higher temperatures to form a thermosetting material.

Another object is to provide a system which rapidly cures at high temperatures.

Another object is to provide a system which is melt stable at 200° C. for several hours, or higher temperatures for shorter periods.

Another object is to provide a compound which can serve as a compatible reactive diluent which will decrease the melt viscosity of phenylethynyl terminated oligomers.

Another object is to provide a compound which is compatible and will increase the crosslink density of phenylethynyl terminated oligomers.

These objects and benefits are achieved according to the present invention by providing a novel composition of matter which is capable of undergoing aromatic nucleophilic substitution and has the general structure

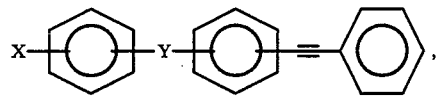

wherein X is F, Cl, or $NO_2$, and Y is an activating group such as CO, $SO_2$, and $C(CF_3)_2$.

Particular compositions having special utility are

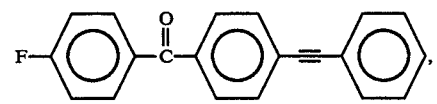

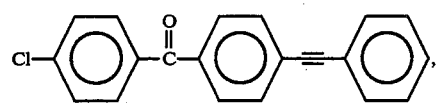

and

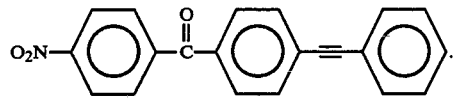

Employing any of the above phenylethynyl compositions to terminate a nucleophilic reagent results in the production of phenylethynyl terminated reactive oligomers exclusively. These phenylethynyl terminated reactive oligomers display unique thermal characteristics, as exemplified by the model compound, 4-phenoxy-4'-phenylethynylbenzophenone, which is relatively stable at 200° C., but reacts at 350° C.

The present invention also comprehends a novel reactive diluent having the general structure

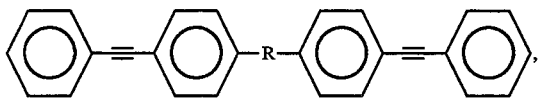

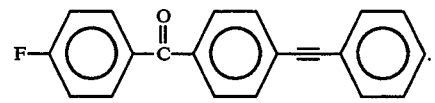

wherein R is any aliphatic or aromatic moiety. This diluent decreases the melt viscosity of the phenylethynyl terminated oligomers discussed above and subsequently reacts therewith to increase density of the resulting thermoset. Particular reactive diluents having special utility are the following compounds:

This organic compound contains a phenylethynyl group as well as an activated aromatic fluoride. The phenylethynyl group is the functionality which reacts at elevated temperatures, while the activated fluoride allows the compound to be incorporated into any system which contains a reactive nucleophile. Thus, since this

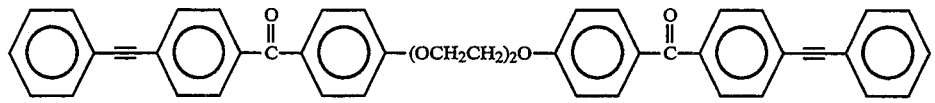

and

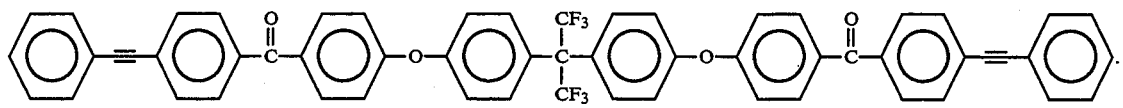

The phenylethynyl terminated reactive oligomers prepared according to the present invention (by employing a novel phenylethynyl composition to terminate a nucleophilic reagent and utilizing a novel reactive diluent to decrease the melt viscosity thereof and subsequently react therewith to increase the crosslink density of the resulting thermoset) have several features which make them attractive candidates for use as composite matrices and adhesives. They are part of an ongoing effort to develop high performance resins for aerospace applications.

BRIEF DESCRIPTION OF THE DRAWINGS

For a more complete understanding of the present invention, including its objects and benefits, reference should be made to the Description of the Preferred embodiments. This Description should be read together with the accompanying drawings, wherein:

FIG. 4 is a graphic representation of the results obtained from the isothermal aging of 4-phenylethynylbenzophenone at 200° C.

DESCRIPTION OF THE PREFERRED EMBODIMENTS

Figure 1:
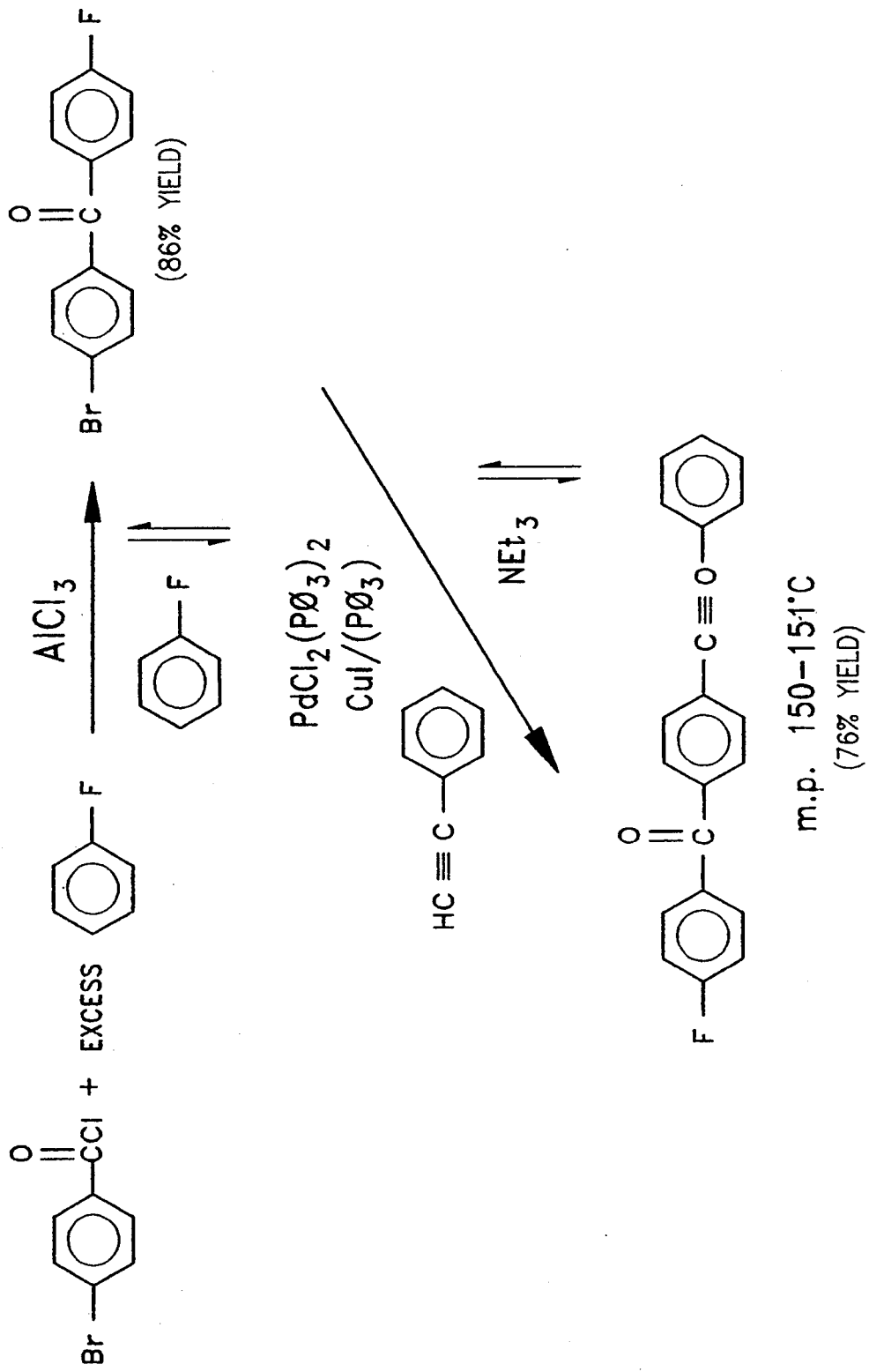
FIG. 1 is an equation showing the synthesis of a reactive endcapping material according to the present invention.
Figure 2:
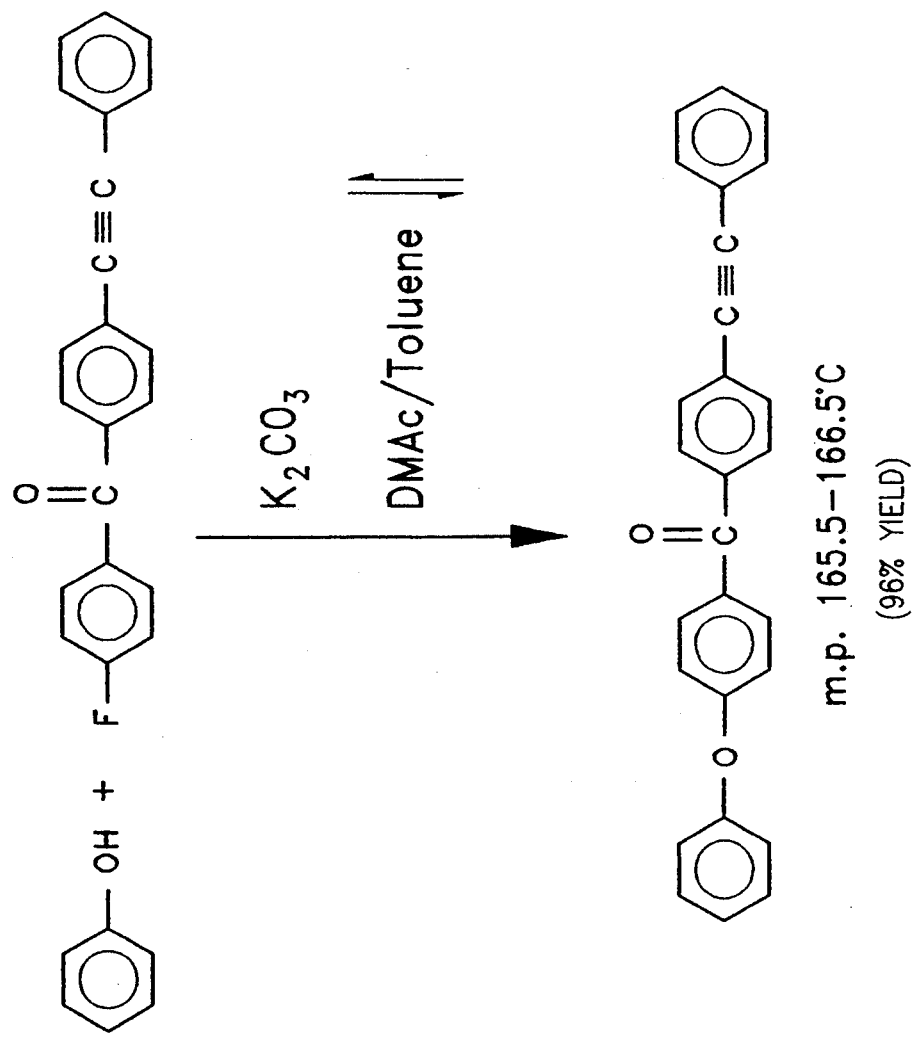
FIG. 2 is an equation showing the synthesis of a phenylethynyl-terminated arylene ether according to the present invention.

The two types of phenylethynyl based compounds described herein are endcappers, and reactive diluents.

The compound 4-fluoro-4'-phenylethynylbenzophenone has the following structural formula:

compound can react by aromatic nucleophilic substitution, any compound having the following general structural formula can also be used as an endcapping agent:

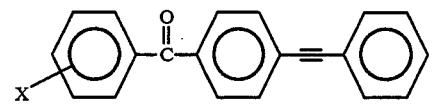

where X is F, Cl, $NO_2$ and Y is CO, $SO_2$, or any other activating group.

The phenylethynyl group has several unexpected advantages over the ethynyl based analog. See the Hergenrother and Delfort references supra. When 4-fluoro-4'-phenylethynylbenzophenone was treated with phenol in the presence of an alkali metal base such as potassium carbonate in a polar aprotic solvent at 160° C., the expected 4-phenoxy-4'-phenylethynylbenzophenone was afforded in nearly quantitative yield. However, when 4-ethynyl-4'-fluorobenzophenone was used in the same procedure, the result was a mixture of products with a total yield of 60%. Several variations in the procedure were tried, but the resulting product was not exclusively the expected ethynyl arylene-ether. This indicates that when the phenylethynyl endcapping compound is used to terminate nucleophilic reagents, the reaction proceeds qualitatively to afford the phenylethynyl terminated reactive oligomers exclusively. If the ethynyl adduct is used, a variety of products results.

A model compound, 4-phenoxy-4'-phenylethynylbenzophenone, is relatively stable at 200° C. as evidenced by little reaction after 20 hours at 200° C., but it reacts in one hour at 350° C. This is unusual since the ethynyl terminated arylene-ethers cure between 160° C. and 250° C. over a one-half to one and one-half hour period. Because these phenylethynyl based compounds display these unique thermal characteristics, a low melting bis(phenylethynyl)arylene-ether was synthesized for use as a reactive diluent. This diluent decreases the melt viscosity of a high molecular weight phenylethynyl terminated oligomer, and subsequently reacts with the oligomer to increase the crosslink density of the resulting thermoset.

Two reactive diluents were prepared by treating two equivalents of 4-fluoro-4'-phenylethynylbenzophenone with one equivalent of either ethylene glycol, or 2,2-bis(4-hydroxyphenyl)hexafluoroisopropylidine in the presence of potassium carbonate in N,N-dimethylacetamide (DMAc) at approximately 170° C. The resulting compounds, 2,2'-bis(4-phenylethynylbenzoyl-4'-phenoxy)ethyl ether and 2,2-bis(4-phenylethynylbenxoyl-4'-phenoxy)hexafluoroisopropylidine, displayed melting points of 127° and 150° C. respectively. These reactive diluents can be used to decrease the melt viscosity of high $T_g$ phenylethynyl-terminated oligomers, thereby improving their melt viscosity, and increasing their crosslink density, modulus, and solvent resistance.

SPECIFIC EXAMPLES

Example 1

Synthesis of 4-fluoro-4'-phenylethynylbenzophenone

In a 250 mL flask equipped with a nitrogen inlet, overhead stirring assembly, and reflux condenser was placed fluorobenzene (117 g, 1.2 mol), and 4-bromobenzyl chloride (39.8 g, 0.181 mol). The mixture was cooled to 0° C. an anhydrous aluminum chloride (27 g, 0.20 mol) was added. The mixture was stirred at 23° C. for 16 hours. The resulting slurry was poured into 2 L of acidic (HCl) water. The organics were extracted with methylene chloride, and dried over magnesium sulfate. The slurry was filtered and the methylene chloride was removed under reduced pressure. Recrystallization from ethanol afforded 43.3 g (86%) of 4-bromo-4'-fluorobenzophenone as white crystals: mp 106°–107° C. (Lit 107°–108° C.).

In a 500 mL flask equipped with nitrogen inlet, overhead stirring assembly, and reflux condenser were placed 4-bromo-4'fluorobenzophenone (30.0 g, 0.107 mol), phenylacetylene (11.0 g, 0.107 mol), triphenylphosphine (0.2 g), copper (I)iodide (0.1 g), bis(triphenylphosphine)palladium (II) chloride (0.1 g), and 450 mL of triethylamine. The mixture was heated to reflux for four hours, then cooled to 23° C. and stirred for an additional 16 hours. The mixture was then poured into acidic (HCl) water, and the precipitate was collected by filtration. Recrystallization from acetone yielded 23 g (75%) of white crystals: mp 150°–151° C. IR (KBr): 2211 cm$^{-1}$ (ethynyl), 1650 cm$^{-1}$ (carbonyl), 1225 cm$^{-1}$ (arylfluorine): H-NMR (CDCl$_3$): 7.8–6.8 ppm (m H aromatic). Anal Calcd for C$_{12}$H$_{13}$OF: %C=83.99, %H=4.36, %F=6.83. Found: %C=83.98, H=4.38, %F=6.16. The structure of this compound is given below:

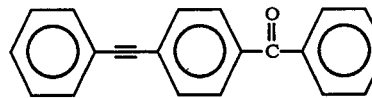

Although the compound contains an activated fluoride, a nitro or chlorine group can also be used to afford an endcapping compound with similar properties.

Example 2

Synthesis of 4-phenoxy-4'-phenylethynylbenzophenone

A 100 mL flask equipped with nitrogen inlet, overhead stirring assembly, Dean-Stark trap, and reflux condenser was charged with phenol (0.35 g, 0.0038 mol), 4-fluoro-4'-phenylethynylbenzophenone (0.10 g, 0.0038 mol) potassium carbonate (0.39 g, 0.003 mol), 25 mL of toluene, and 50 mL of DMAc. The mixture was heated to reflux and water was removed by azeotropic distillation, followed by the removal of toluene over a 20 hour period. The reaction was cooled to 23° C., and the mixture was poured into 1 L of acidic (HCl) water. The precipitate was collected by filtration to afford 1.37 g (96%) of 4-phenoxy-4'-phenylethynylbenzophenone as a white powder: mp 165.5° C. IR (KBr): 2216 cm$^{-1}$ (ethynyl), 1650 cm$^{-1}$ (carbonyl): $^1$H-NMR (CDCl$_3$): 7.8–6.8 pp, (m H aromatic). Anal Calcd. for C$_{27}$H$_{18}$O$_2$: %C=86.61, %H=4.85. Found: %C=86.46, %H=4.68. The structure of this compound is given below:

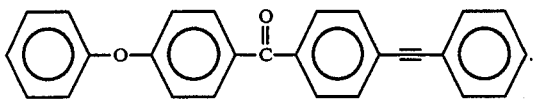

Figure 3:
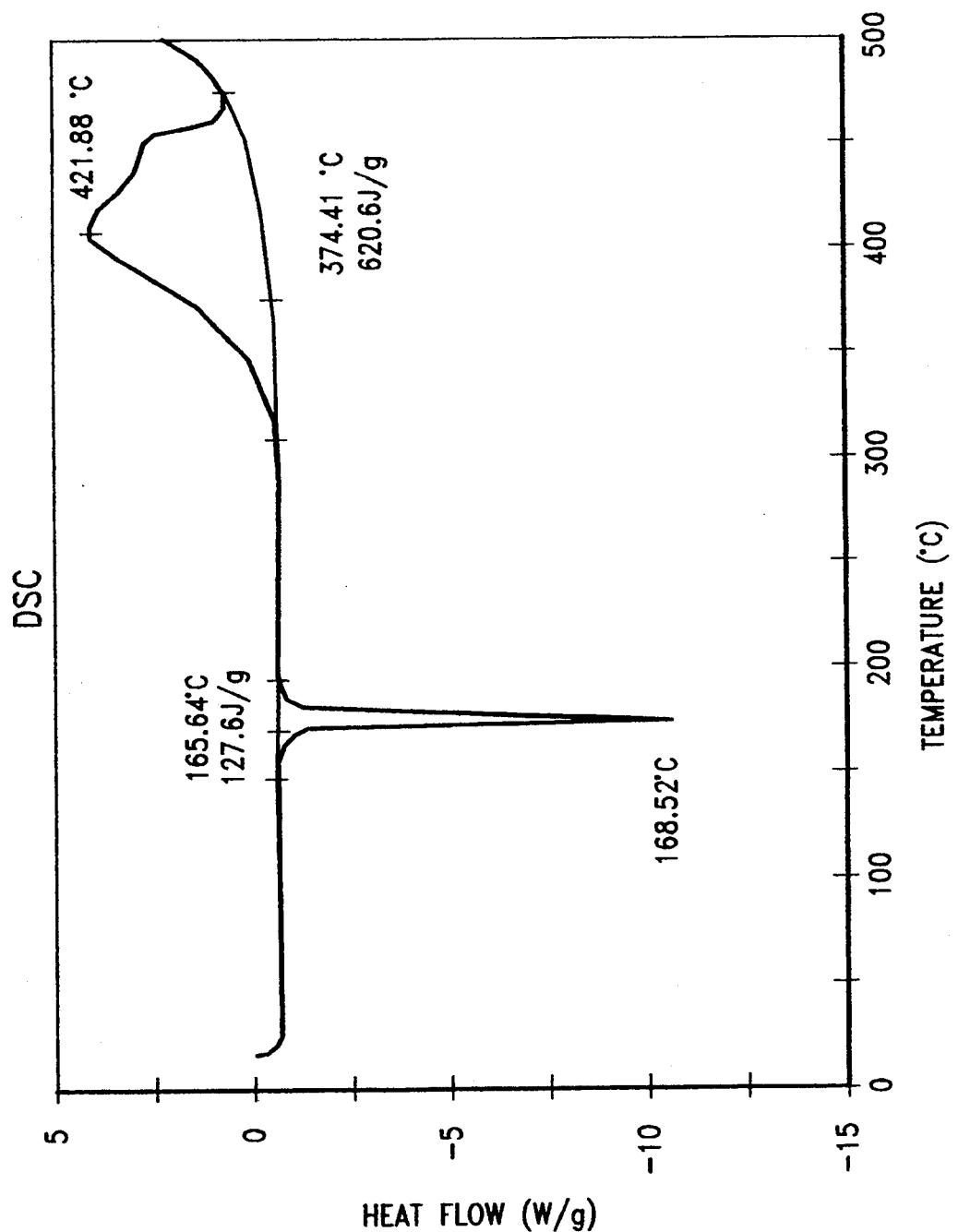
FIG. 3 is a Differential Scanning Calorimetry (DSC) thermogram of 4-phenoxy-4'-phenylethynylbenzophenone prepared according to the present invention in examples 1 and 2.

The DSC thermogram of this compound is presented in FIG. 3.

Synthesis of 2,2'-bis(4-phenylethynylbenzoyl-4'-phenoxy)ethyl ether (PEBPE)

In a 100 mL flask equipped with a nitrogen inlet, overhead stirring assembly, and reflux condenser was placed 4-fluoro-4'-phenylethynylbenzophenone (11.09 g, 0.0369 mol) ethylene glycol (1.96 g, 0.0185 mol), potassium carbonate (15.3 g, 0.111 mol) and 80 mL of DMAc. The reaction was heated to reflux for 16 hours, cooled to 23° C. and poured into 2 L of water. The resulting precipitate was stirred for eight hours, then collected by filtration and dried in vacuo at 110° C. The yield of white powder was 12.06 g (97%) mp (DSC) 127° C. IR (KBr): 2875 cm$^{-1}$ (methylene), 2216 cm$^{-1}$ (ethynyl), 1643 cm$^{-1}$ (carbonyl), 1069 cm$^{-1}$ (aryl-aliphatic ether). The structure of this compound is given below:

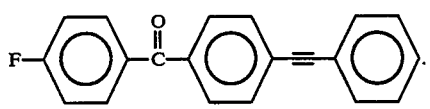

Example 3

Synthesis of 2,2'-bis(4'-phenylethynylbenzoyl-4'-phenoxy)diphenylhexafluoroisopropylidine (PEBD-6F)

In a 100 mL flask equipped with a nitrogen inlet, overhead stirring assembly, Dean-Stark trap, and reflux condenser was placed 2,2-bis(4-hydroxyphenyl)hexafluoroisopropylidine (2.3537 g, 0.007 mol), 4-fluoro-4'-phenylethynylbenzophenone (4.2047 g, 0.014 mol), potassium carbonate (2.13 g, 0.0154 mol), toluene (30 mL), and DMAC (37 mL). The mixture was heated to reflux and water removed by azeotropic distillation, followed by the removal of toluene over an eight hour period. The reaction was cooled to 23° C. and poured into water. The precipitate was collected by filtration and dried in vacuo at 100° C. to afford 6.1 g (>95%) of light yellow powder: mp (DSC) 150° C. IR (KBr): 3066–0326 cm$^{-1}$ (aromatic H), 2214 cm$^{-1}$ (C≡C), 1651 cm$^{-1}$ (C=O), and 1248 cm$^{-1}$ (CF$_3$).

The structure of this compound is given below:

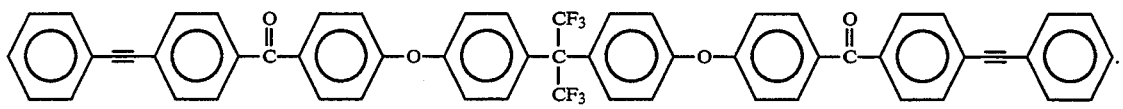

Example 4

General Procedure for the Preparation of Poly(arylene ether) Blends Containing Phenylethynl Reactive Diluents In a 50 mL flask was placed tetrahydrofuran (5 mL), a 6000 g/mol phenylethynyl-terminated arylene ether and a reactive diluent to create 16% (w/v) solids solution containing a ratio of 10 and 30% by weight reactive diluent/arylene ether oligomer blends. The solution was stirred for one-half hour after all the solids dissolved, then poured into water. The precipitate was collected by filtration and dried in vacuo at 100° C. for eight hours.

Example 5

4-Phenoxy-4'-phenylethynylbenzophenone was placed in a DSC cell and heated at a rate of 20° C./rain to 450° C. The compound displayed a mp at 165° C. with a melting enthalpy of 127 J/g, and an exothermic onset at 320° C. with a maximum onset at 421° C. The DSC thermogram for this example is shown in FIG. 3.

Example 6

Figure 4A:
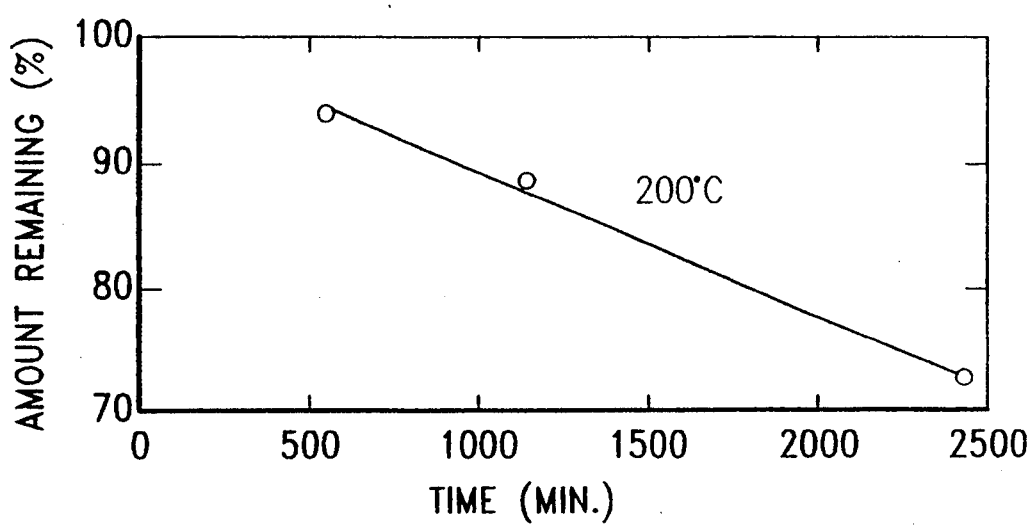
(FIG. 4A) and at 250°, 275°, and 300° C.
Figure 4B:
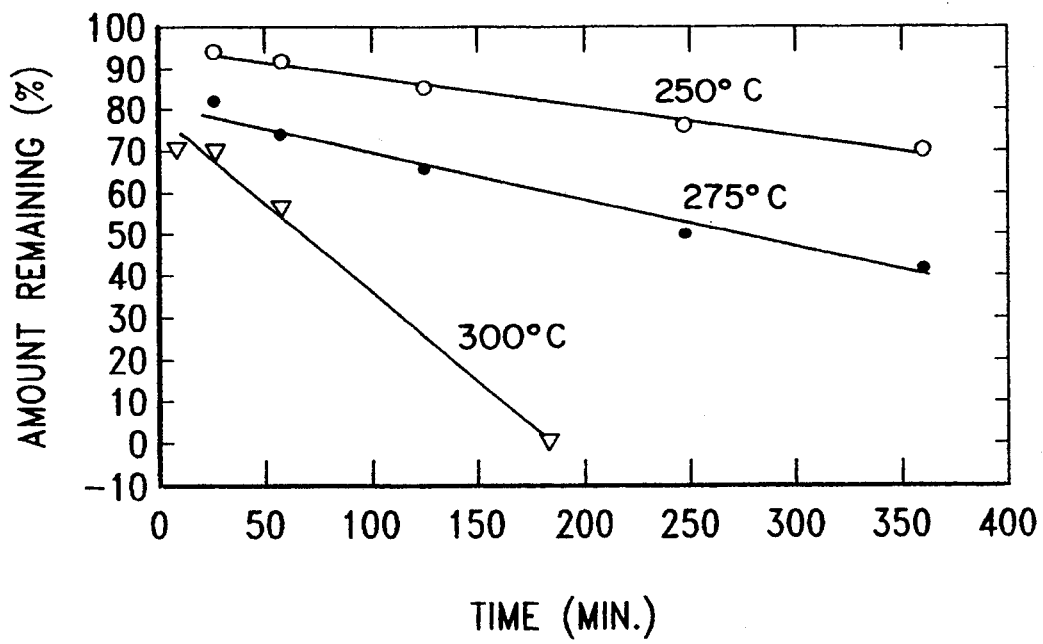
(FIG. 4B)

Several samples of 4-phenoxy-4-'-phenylethynylbenzophenone were held isothermally at 200°, 250°, 275°and 300° C. These samples were then reheated at a rate of 20° C./rain in a DSC cell. The melting enthalpies of these samples were then compared to the melting enthalpy of the pure compound (FIG. 3), and a plot of the percent amount remaining versus time at temperature was generated to demonstrate the thermal stability of the phenylethynyl group. See FIGS. 4A and 4B.

Example 7

Figure 5:
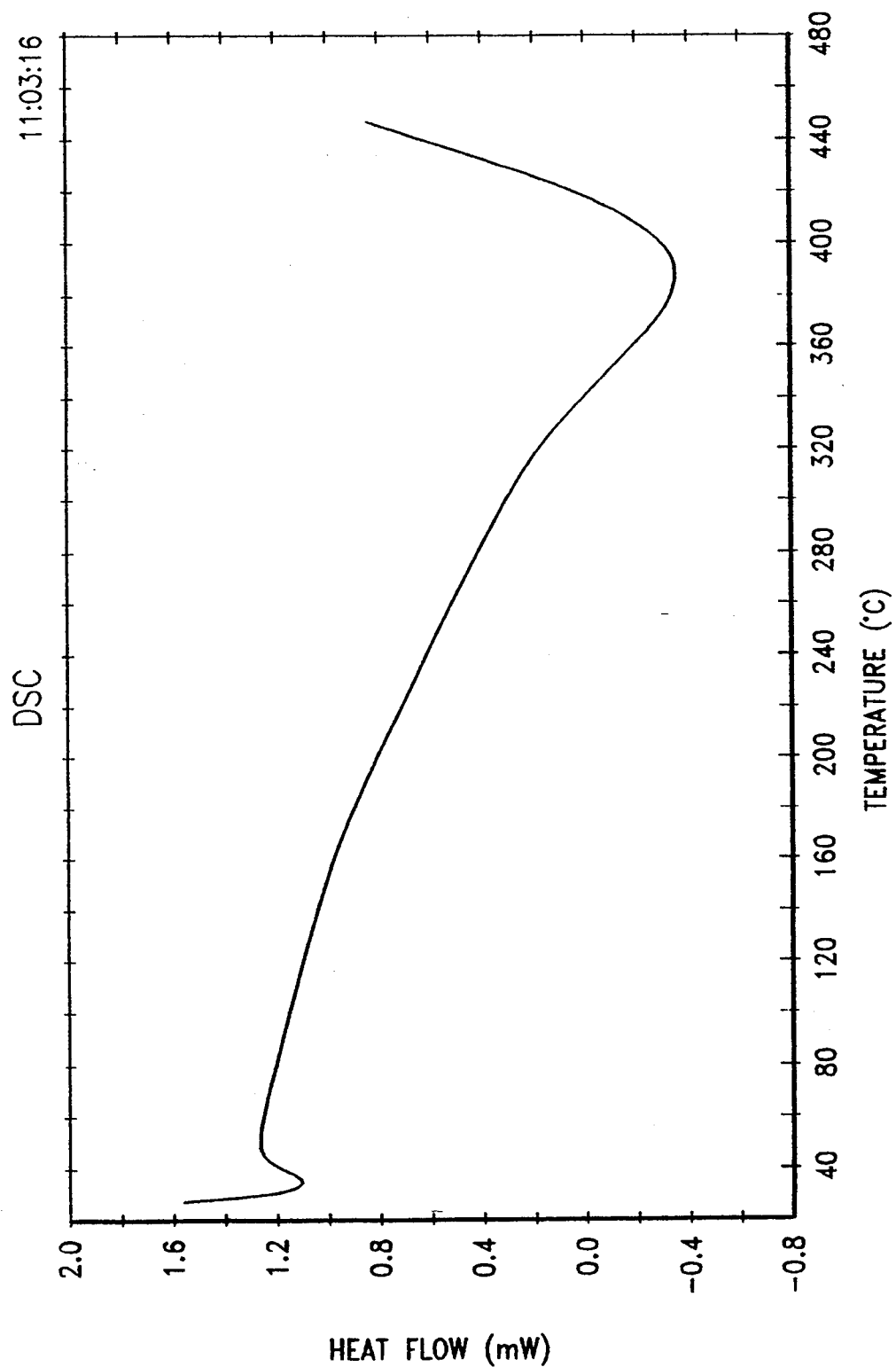
FIG. 5 is a DSC thermogram of 4-phenoxy-4'-phenylethynylbenzophenone after being held at 350° C. for one hour.

4-Phenoxy-4'-phenylethynylbenzophenone was placed in a DSC cell and held at 350° C. for one hour. The compound was then rapidly cooled and reheated at a rate of 20° C./rain to 500° C. The compound displayed a smooth baseline and an absence of both a melting point, and an exothermic peak. The DSC thermogram for this example is shown in FIG. 5.

Example 8

Blends were prepared from both reactive diluents, 2,2'-bis(4-phenylethynylbenzoyl-4-'phenoxy)ethyl ether (PEBPE) and 2,2'-bis(4-phenylethynylbenzoyl-4'-phenyoxy)diphenylhexafluoroisopropylidine (PEBD-6F), with a 6000 g/mol phenylethynyl terminated arylene ether, Tg=215° C., to afford a ratio of 10 and 30% by weight reactive diluent/arylene ether oligomer blends. The blends were pressed into ¾ in. circular disks and placed between two rotating parallel plates. The results of the complex melt viscosities as a function of temperature for these blends are shown on the following table.

| | Complex Viscosities of Phenylethynyl Terminated Poly(arylene ether) Blends | | | | |
|---|---|---|---|---|---|
| Temperature (°C.) | Poly(arylene ether) Melt Viscosity (Pa)$^a$ | PEBPE Blend Melt Viscosity (Pa) | | PEBD-6F Blend Melt Viscosity (Pa) | |
| | | 10% (w) | 30% (w) | 10% (w) | 30% (w) |
| 160 | Solid | 2.3 × 10$^6$ | 2.3 × 10$^4$ | 9.2 × 10$^5$ | 7.7 × 10$^5$ |
| 200 | Solid | 17000 | 3360 | 4.7 × 10$^5$ | 1.4 × 10$^5$ |
| 260 | 2.8 × 10$^5$ | 4370 | 480 | 6.3 × 10$^4$ | 6830 |
| 276 | 4.3 × 10$^5$ | 860 | 230 | 4.4 × 10$^4$ | 1400 |
| 300 | 4 × 10$^4$ | 280 | 200 | 1.0 × 10$^4$ | 1300 |

$^a$6000 g/mol phenylethynyl terminated oligomer T$_g$ = 215° C.

We claim:
1. A phenylethynyl terminated reactive oligomer prepared from the reaction of a phenol and a composition having the formula:

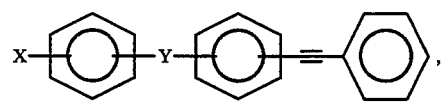

wherein X is selected from the group consisting of F, Cl, and NO$_2$, and Y is selected from the group consisting of CO, SO$_2$ and C(CF$_3$)$_2$.

* * * * *